(12) United States Patent
Araishi

(10) Patent No.: US 11,819,707 B2
(45) Date of Patent: Nov. 21, 2023

(54) LIGHT THERAPY DEVICE AND ELECTRODE ROD

(71) Applicant: DR-COCOS Corporation, Kasuga (JP)

(72) Inventor: Yasuto Araishi, Kasuga (JP)

(73) Assignee: DR-COCOS Corporation, Kasuga (JP)

( * ) Notice: Subject to any disclaimer, the term of this patent is extended or adjusted under 35 U.S.C. 154(b) by 0 days.

(21) Appl. No.: 17/800,899

(22) PCT Filed: Mar. 8, 2022

(86) PCT No.: PCT/JP2022/010071
§ 371 (c)(1),
(2) Date: Aug. 19, 2022

(87) PCT Pub. No.: WO2023/170798
PCT Pub. Date: Sep. 14, 2023

(65) Prior Publication Data
US 2023/0310881 A1 Oct. 5, 2023

(51) Int. Cl.
*A61N 5/06* (2006.01)
(52) U.S. Cl.
CPC .... *A61N 5/0624* (2013.01); *A61N 2005/0662* (2013.01); *A61N 2005/0665* (2013.01)
(58) Field of Classification Search
CPC ..................................... A61N 5/06–2005/073
See application file for complete search history.

(56) References Cited

U.S. PATENT DOCUMENTS

2006/0112331 A1    5/2006  Ashida et al.

FOREIGN PATENT DOCUMENTS

| JP | S53-83360 A | 7/1978 |
| JP | S59-160950 A | 9/1984 |
| JP | 3110522 U | 6/2005 |

OTHER PUBLICATIONS

International Search Report for PCT/JP2022/010071 dated May 10, 2022.
PCT written opinion dated May 10, 2022.
Japanese decision to grant a patent dated Apr. 5, 2023.

*Primary Examiner* — Jonathan T Kuo
(74) *Attorney, Agent, or Firm* — Yokoi & Co., U.S.A.; Toshiyuki Yokoi

(57) ABSTRACT

A light generated by arc discharge is efficiently and widely used for preventing and treating diseases such as viral infectious disease by optimally enhancing and adjusting a wavelength region of light of a light therapy device and increasing usability of the light therapy device. A light therapy device includes: a pair of electrodes containing carbon, titanium nitride and at least one of potassium and potassium compounds; a support portion for supporting the pair of electrodes so that the pair of electrodes is arranged at a predetermined distance from each other; and an electric circuit configured to apply a voltage between the pair of electrodes for generating arc discharge between the pair of electrodes.

7 Claims, 16 Drawing Sheets

1

LIGHT THERAPY DEVICE AND ELECTRODE ROD

TECHNICAL FIELD

The present invention relates to a light therapy device (phototherapy device) which generates arc discharge between a pair of electrodes and uses rays of light generated by arc discharge for preventing and treating diseases such as viral infectious disease and an electrode rod used for the light therapy device.

BACKGROUND ART

Conventionally, in the electrode rod used for the light therapy device generating arc discharge, since an emission intensity is very weak when using the electrode containing only carbon, the electrode rod containing also some kinds of metal is known for enhancing the emission intensity. Patent document 1 discloses that adding a lanthanoid rare earth compound such as cerium and lanthanum or an alkali metal to carbon leads to enhancing the emission intensity.

An emission spectrum of light (beam, ray) generated by arc discharge is changed by adding metal in the electrode rod. This is because metal shows the emission spectrum having its own wavelength region depending on the element of metal. The width of the peak in spectrum is approximately same and narrow regardless of the type of the element when a single element is used. In addition, the number of the emission peaks (wavelengths) is basically one when the added metallic element is one. In the conventional electrode rod, the type of metal to be added is limited. Thus, the number of the emission peaks and the width of the wavelength region of each of the emission peaks cannot be increased or extended exceeding the region of the added metallic element. Furthermore, the usage of the conventional light therapy device is limited. For example, the conventional light therapy device is used for a thermotherapy for reducing a pain, improving circulation and adjusting circadian rhythm.

PRIOR ART DOCUMENTS

Patent Documents

[Patent document 1] Japanese Patent Application Publication No. S53-083360

DISCLOSURE OF THE INVENTION

Problems to be Solved by the Invention

In the conventional light therapy device, there is no thought of adjusting the emission spectrum of light generated by arc discharge. Thus, the light therapy device using arc discharge is not efficiently used for purposes other than the limited purpose. The present invention aims for efficiently and widely using rays of light generated by arc discharge for preventing and treating diseases such as viral infectious disease by optimally enhancing and adjusting the wavelength region of the light and increasing usability of the light therapy device.

Considering safety at high temperature of arc discharge and harmful influence on human body, the types of the metallic element that can be actually used for the electrode rod are considerably limited. For example, as for a nonmetal carbon, fume of carbon nanotube processed at a high temperature may cause fibroid lung if it is inhaled into the human body. Thus, pure carbon or graphite is preferable. Although silicon compound emits the infrared rays, the silicon compound cannot be used for arc discharge since there is a risk of pneumoconiosis and carcinogenicity. A compound multiply containing many harmful elements such as calcium halo-phosphate cannot be used for the light therapy device although it is used for a fluorescent lamp used in an environment sealed by a glass. As described above, consideration of the harmful influence on the human body is required for adding metal to the electrode rod.

Means for Solving the Problem

A light therapy device of the present invention includes: a pair of electrodes containing carbon, titanium nitride and at least one of potassium and potassium compounds; a support portion for supporting the pair of electrodes so that the pair of electrodes is arranged at a predetermined distance from each other; and an electric circuit configured to apply a voltage between the pair of electrodes for generating arc discharge between the pair of electrodes. In the light therapy device configured above, since titanium nitride is added to the electrodes, the light emission having a plurality of increased emission peaks can be achieved by using the absorption/scattering effect of light and plasmon effect. The light having the extended width of the wavelength region covering the ultraviolet region is irradiated. Thus, the effect against viral and bacterial infections can be exhibited. From the fact that titanium nitride is used for an artificial joint and the like, it is considered that titanium nitride has high biocompatibility and the harmful influence on the human body is little.

In the above described configuration, the pair of electrodes can further contain at least one of silver and calcium. In the light therapy device configured above, since silver or calcium is added to the electrodes, the emission intensity is enhanced at the near infrared region. Thus, the therapeutic effect to the biological body can be increased. In addition, the harmful ultraviolet wavelength of UV-B and UV-C can be reduced.

In the above described configuration, an adsorbent configured to adsorb carbon dioxide generated by arc discharge can be further provided, and the adsorbent can contain clay powder, wood ash, charcoal and zeolite. In the light therapy device configured above, carbon dioxide and the oxide of metal generated by combustion are adsorbed by the adsorbent. Thus, the generated substance is prevented from being directly inhaled into the user or being directly discharged to the outside.

In the above described configuration, a fan installed in a vicinity of the pair of electrodes for introducing carbon dioxide to the adsorbent can be further provided. In the light therapy device configured above, the adsorption of carbon dioxide and the oxide of metal to the adsorbent can be facilitated.

In the above described configuration, the electric circuit can include a MOSFET or an IGBT. In the light therapy device configured above, the size and weight can be reduced compared to the case of using a conventional large-sized transformer. Consequently, the light therapy device can be easily carried.

In the above described configuration, a reflector made of metal for reflecting light generated by arc discharge can be further provided, and a groove can be formed on the reflector. In the light therapy device configured above, the intensity of light can be enhanced. Thus, the light can be generated with the minimum electric power.

Effects of the Invention

In the present invention, using rays of light generated by arc discharge can lead to efficiently and widely preventing and treating diseases such as viral infectious disease.

MODE FOR CARRYING OUT THE INVENTION

Figure 1:
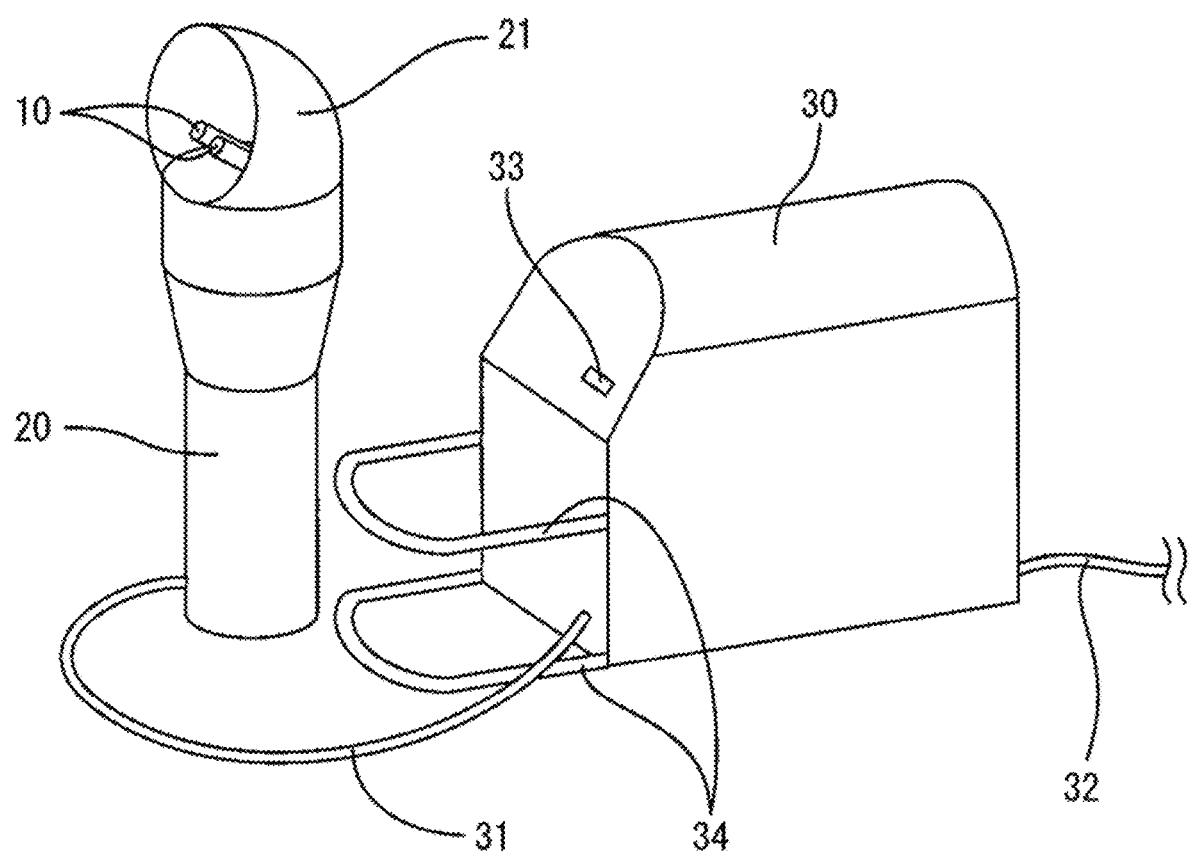
FIG. 1 is a perspective view of a light therapy device of an embodiment of the present invention.

Hereafter, embodiments of the present invention will be explained with reference to the drawings shown as an example. FIG. 1 is a perspective view of a light therapy device 1 of an embodiment of the present invention. The light therapy device 1 is a portable therapy device which is small-sized, light-weighted and easily portable. As shown in FIG. 1, the light therapy device 1 is formed by a pair of electrode rods 10, an irradiation portion 20 configured to be movable by being held by a hand of a user and a body portion 30 housing an electric circuit and the like inside, for example. The pair of electrode rods 10 is arranged near the tip end of the irradiation portion 20 so that the pair of electrode rods 10 is arranged at a predetermined distance from each other. A hood 21 partly covers a periphery the electrode rods 10. The body portion 30 includes a connection cable 31 for electrically connecting the irradiation portion 20 and the body portion 30, a power cable 32 for connecting the body portion 30 to a power source, a power switch 33 for switching ON/OFF the power source, a housing portion 34 for housing the irradiation portion 20 near the body portion 30 in a standing state, for example.

The voltage is applied to the pair of electrode rods 10 by the electric circuit installed in the body portion 30. Thus, arc discharge is generated between the pair of electrode rods 10 and the light is generated by arc discharge. The generated light is irradiated from an opening portion of the hood 21 to a body or the like of the user. Thus, the emission energy of the light is used for preventing and treating diseases such as viral infectious disease.

Figure 2:
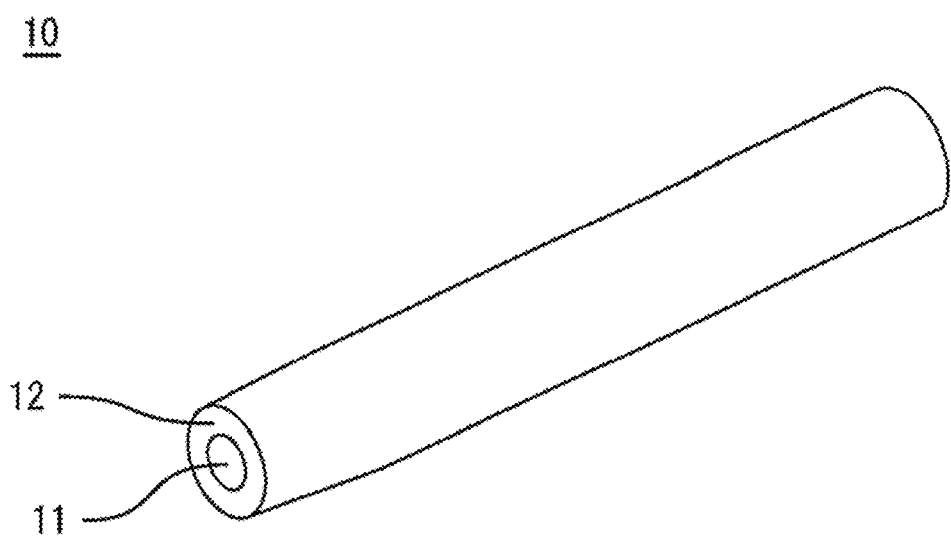
FIG. 2 is a perspective view of an electrode rod used for the light therapy device.

FIG. 2 is a perspective view of the electrode rod 10 used for the light therapy device 1. As shown in FIG. 2, the electrode rod 10 is formed by a core material portion 11 having a columnar (cylindrical) shape for generating arc discharge and an aggregate material portion 12 for surrounding a periphery of the core material portion 11 to protect the core material portion 11. The aggregate material portion 12 is manufactured by mixing carbon aggregate such as petroleum coke and graphite powder with a binder such as tar and thermosetting resin and burning the mixture at 1000° C. to solidify it. For improving combustibility, 20 to 30% of sulfur can be mixed. The aggregate material portion 12 is designed in a cylindrical rod shape having a diameter of approximately 5 to 10 mm. A center portion of the aggregate material portion 12 is hollowed out by approximately 2 mm, a mixture of the materials of the core material portion 11 is injected into a hollow portion and burning the aggregate material portion 12 with the core material portion 11 again to solidify the core material portion 11. The core material portion 11 is formed by mixing fine power of potassium carbonate, iron, titanium nitride, calcium carbonate, cerium oxide, lanthanum oxide and silver together with a binder such as petroleum pitch and tar, for example. An example of the mixing ratio of the material forming the core material portion 11 is shown in Table 1. As for the titanium nitride, fine particles having a particle diameter of 1 to 1.5 μm is used. It is also possible to use potassium or other potassium compounds instead of potassium carbonate. It is also possible to use calcium or other calcium compounds instead of calcium carbonate.

TABLE 1

| material | mixing ratio (weight %) |
| --- | --- |
| potassium carbonate ($K_2CO_3$) | 5-15 |
| iron (Fe) | 10-20 |
| titanium nitride (TiN) | 10-30 |
| calcium carbonate ($CaCO_3$) | 5-10 |
| cerium oxide ($CeO_2$) | 5-30 |
| lanthanum oxide ($La_2O_3$) | 5-20 |
| silver (Ag) | 5-10 |

Figure 3:
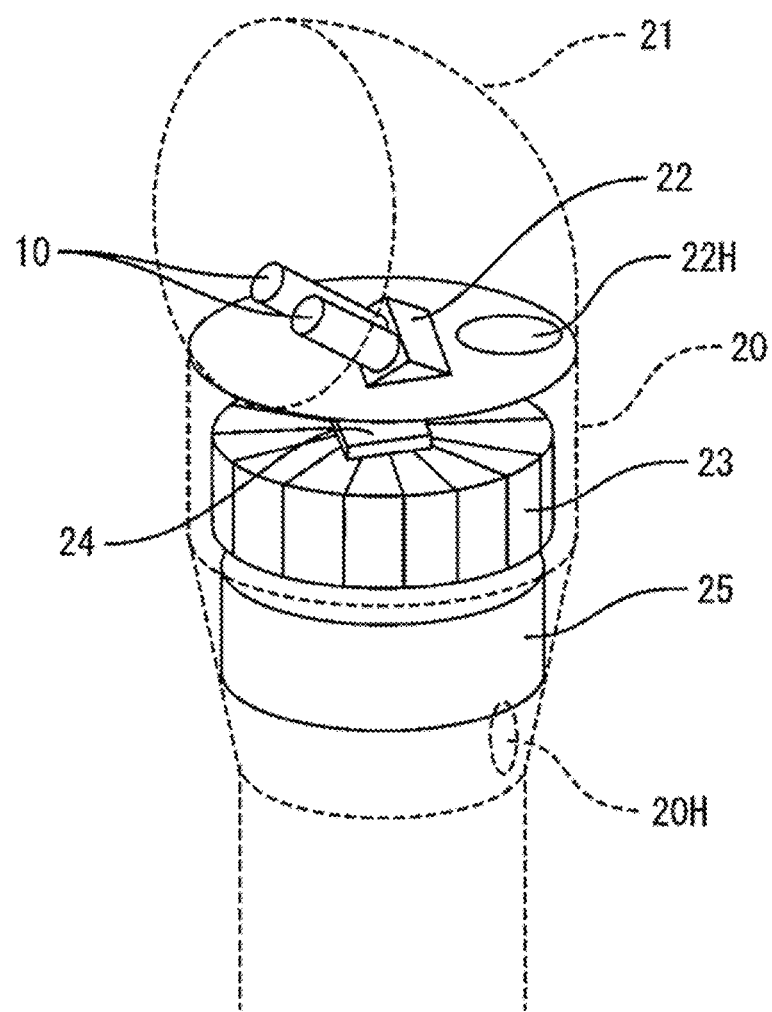
FIG. 3 is a drawing showing an internal structure of an irradiation portion in which the electrode rod is arranged.

FIG. 3 is a drawing showing an internal structure of the irradiation portion 20 in which the pair of electrode rods 10 are arranged. An outer part of the irradiation portion 20 is shown by broken lines and the structures arranged inside are shown by solid lines. The irradiation portion 20 includes a hood 21, a support portion 22, a fan 23, a thermoelectric cooler 24 and an adsorption portion 25. The support portion 22 has a shape where an inclined surface is provided on a disk-shaped plate. The pair of electrode rods 10 is inserted through the support portion 22 from downward to upward. Thus, the pair of electrode rods 10 is supported in a state that the pair of electrode rods 10 is protruded from an upper surface of the plate. The pair of electrode rods 10 is arranged so as to be directed obliquely upward by optimally specifying the angle of the inclined surface. The protruded lengths of the electrode rods 10 from the support portion 22 are constant. The electrode rods 10 are fixed to the support portion 22 in a state of being arranged while being separated at a predetermined distance from each other. A thorough hole 22H is provided on the plate of the support portion 22. Carbon dioxide and the metals generated by arc discharge are passed through the thorough hole 22H and introduced into the fan 23, the adsorption portion 25 and the like.

The thermoelectric cooler 24 is a device for converting heat into electricity using a Peltier element. The thermoelectric cooler 24 is arranged on a lower part of the electrode rods 10. Thus, the heat generated by arc discharge is cooled and the fan 23 is driven by using the electricity generated by the thermoelectric cooler 24. A heat absorption side of the thermoelectric cooler 24 is directed toward the electrode rods 10 (upward) and a heat radiation side of the thermoelectric cooler 24 is arranged closely to a heat radiator of the fan 23. The fan 23 is driven by a motor incorporated in the fan 23 to generate wind. Thus, a circumference of the electrode rods 10 is cooled. In addition, the gas (including carbon dioxide, oxide of metal and the like) generated by arc discharge is introduced to the adsorption portion 25 and the gas passed through the adsorption portion 25 is facilitated to be discharged to the outside from an exhaust hole 20H provided on a side surface of the irradiation portion 20. It is also possible to connect the fan 23 directly with the power source without using the thermoelectric cooler.

Figure 4:
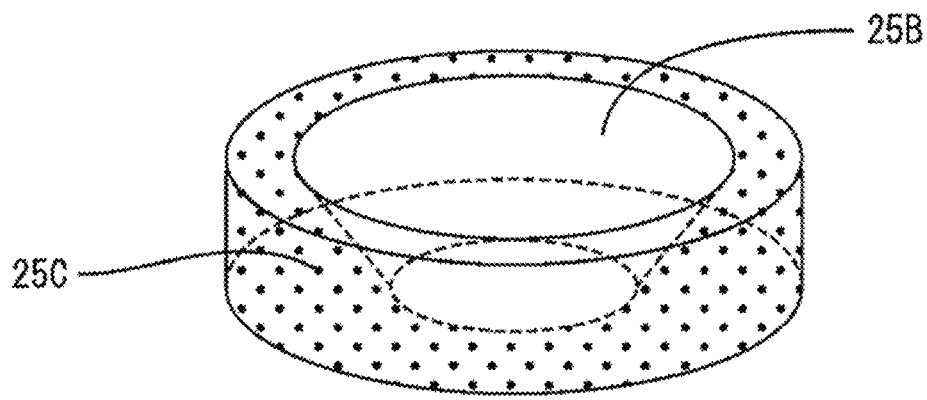
FIG. 4 is a drawing schematically showing a structure of an adsorbent.
Figure 4:
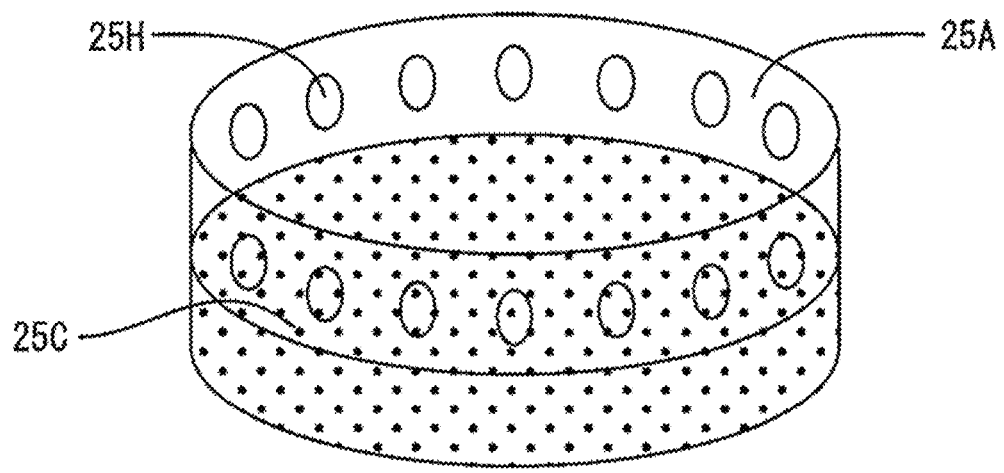

The adsorption portion 25 is arranged on a lower part of the fan 23. The adsorption portion 25 is a portion for adsorbing the gas such as carbon dioxide and metallic oxide generated by combustion (arc discharge). FIG. 4 is a drawing schematically showing the structure of the adsorption portion 25. As shown in FIG. 4, the adsorption portion 25 is formed by case portions 25A, 25B and an adsorbent 25C. A lower part of the case portion 25A and an inside of the case portion 25B are filled with the adsorbent 25C. The case portion 25B has a structure formed by combining an outer cylinder having a columnar shape and an inner cylinder having a funnel shape (triangular pyramid shape). The adsorbent 25C is arranged between the inner cylinder and the outer cylinder. The diameter of the inner cylinder having a funnel shape is gradually reduced from an upper side to a lower side. The inner cylinder is opened at the bottom end of the case portion in a circular shape. Namely, the case portion 25B includes an opening portion penetrating through the case portion 25B in the vertical direction. In a state that the adsorbent 25C is arranged in the case portion 25A, the case portion 25B is arranged on an upper part and an inside of the case portion 25A. The gas and the like entered in the case portion 25B from the above passes through the adsorbent 25C filled in the case portion 25B. The gas sent out downward passes through the adsorbent 25C filled in the case portion 25A. At that time, carbon dioxide, the oxide of metal and the like contained in the gas is adsorbed by the adsorbent 25C. Consequently, harmful substance can be removed from the gas discharged to the outside from the exhaust hole 20H. A plurality of holes 25H is formed on an outer periphery of an upper part of the case portion 25A. Thus, the gas passing through the adsorbent 25C is facilitated to be discharged from the exhaust hole 20H. It is not necessary to use both the case portion 25A and the case portion 25B in combination. It is also possible to use only one of the case portion 25A and the case portion 25B.

For the condition of the adsorbent, it is required that the adsorbent can be easily replaced when the number of times of use exceeds a predetermined number, the adsorbent can adsorb harmful substance quickly, the adsorbent can be manufactured easily, the adsorbent is durable to a high temperature, the adsorbent is odorless, the adsorbent is safe material and the adsorbent does not discharge the adsorbed gas and the like easily. In addition, consideration is required for the material of the adsorbent not to contain the metal such as lithium which may cause environmental pollution of soil, river and the like so that the adsorbent after the use can be disposed at an ordinary home. The material and the manufacturing method of the adsorbent 25C developed based on the above described viewpoint will be explained. The material of the adsorbent 25C is manufactured by mixing charcoal (wood charcoal) and zeolite by the volume ratio of 2:1 to 1:1, crushing the mixture into powder, mixing the powder of ash and feldspar by the volume ratio of 0.5:1 to 0.5:2, mixing a small amount of water and alkaline electrolytic water and adding silica gel by the volume ratio of approximately 1 to 2.5 after the moisture is adequately contained in the mixture. The ash is wood ash, for example. The ash contains potassium, magnesium and calcium. The feldspar is white clay powder used when manufacturing pottery. The feldspar contains silica by 70 to 80%, aluminum oxide by 18 to 25%, potassium oxide by 5 to 12%, sodium oxide by 3 to 10%, iron oxide by 0.1%, calcium oxide by 0.1 to 0.2% and magnesium oxide by 0.01 to 0.05%, for example. The feldspar is mined in India, Japan and all over the world. The composition of the feldspar is slightly different depending on the place of production. Since the content of the calcium oxide in the feldspar is small compared to other components, the calcium oxide can be further added to the feldspar to increase the adsorption efficiency. Instead of the feldspar, it is also possible to use a combination of mixing several kinds of clay powders used for pottery where the content of the potassium oxide, the sodium oxide, the calcium oxide, the magnesium oxide and the like is mainly increased. As for the reaction with carbon dioxide, the potassium oxide is converted into the potassium carbonate, the sodium oxide is converted into the sodium carbonate and the calcium oxide converted into the calcium carbonate, as shown below.

$$K_2O + H_2O \rightarrow 2KOH$$

$$2KOH + CO_2 \rightarrow K_2CO_3 + H_2O$$

$$Na_2O + H_2O \rightarrow 2NaOH$$

$$2NaOH + CO_2 \rightarrow Na_2CO_3 + H_2O$$

$$CaO + H_2O \rightarrow Ca(OH)_2$$

$$Ca(OH)_2 + CO_2 \rightarrow CaCO_3 + H_2O$$

The alkaline electrolytic water is generated at the negative side when water or salt solution is electrolyzed. Table 2 shows an example of the composition of the adsorbent 25C by weight.

TABLE 2

| material | weight (g) |
|---|---|
| zeolite | 20 |
| wood charcoal | 10 |
| ash | 4 |
| feldspar (clay powder) | 20 |
| silica gel | 15 |
| water | 30-35 |
| alkaline electrolytic water | 1 |

Figure 5:
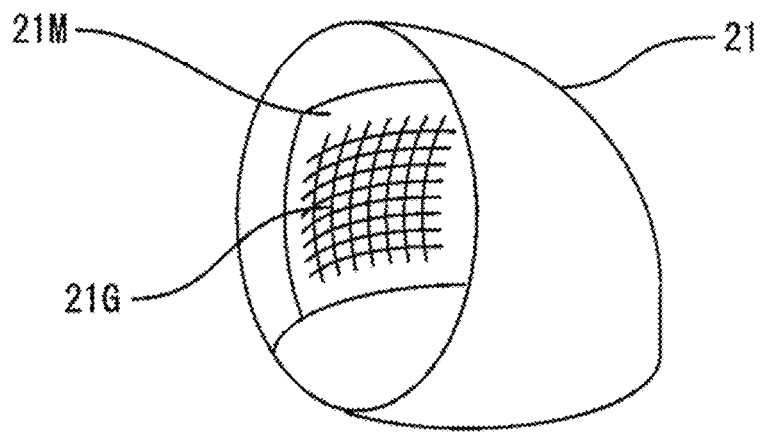
FIG. 5 is a drawing schematically showing an optical energy enhancing mechanism formed on a reflector.

FIG. 5 is a drawing schematically showing an optical energy enhancing mechanism formed on a reflector. In FIG. 5, as the optical energy enhancing mechanism, a reflector 21M made of metal (stainless) is arranged inside the hood 21 and grooves 21G are formed on a surface of the reflector 21M. Since the reflector 21M is arranged, the light generated by arc discharge is reflected to increase the amount of the light emitted to the user side. Thus, the energy is enhanced. In addition, since the grooves 21G are formed on the surface of the reflector 21M, the strength of light can be enhanced by the actions of refraction/reflection and radiation of the light. The grooves 21G are formed by vertical and horizontal grooves parallelly arranged with the width of approximately 100 μm so that the vertical grooves and the horizontal grooves are orthogonal to each other. The width between the grooves is not limited to the above described width. It is not necessary to form the grooves to be parallel with each other. In addition, it is not necessary to form the grooves in a lattice shape. It is also possible to form only the vertical grooves or only the horizontal grooves. It is also possible to form the grooves in a honeycomb shape. The intensity of the light energy can be adjusted by changing the number, the length, the depth, the shape, the arrangement and the combination of the grooves. Thus, the light therapy device 1 can be more efficiently used. Note that the formation of the grooves 21G means to form recessed lines or projected parts on the surface of the reflector 21M. The effect of enhancing the energy can be also obtained by thinly coating the surface of the reflector 21M with aluminum or silver. In addition, the portion of forming the reflector 21M and the grooves 21G is not limited to the hood 21. The reflector 21M and the grooves 21G can be also formed on the support portion 22 for supporting the electrode rods 10 or other portions located near the light source.

Figure 6:
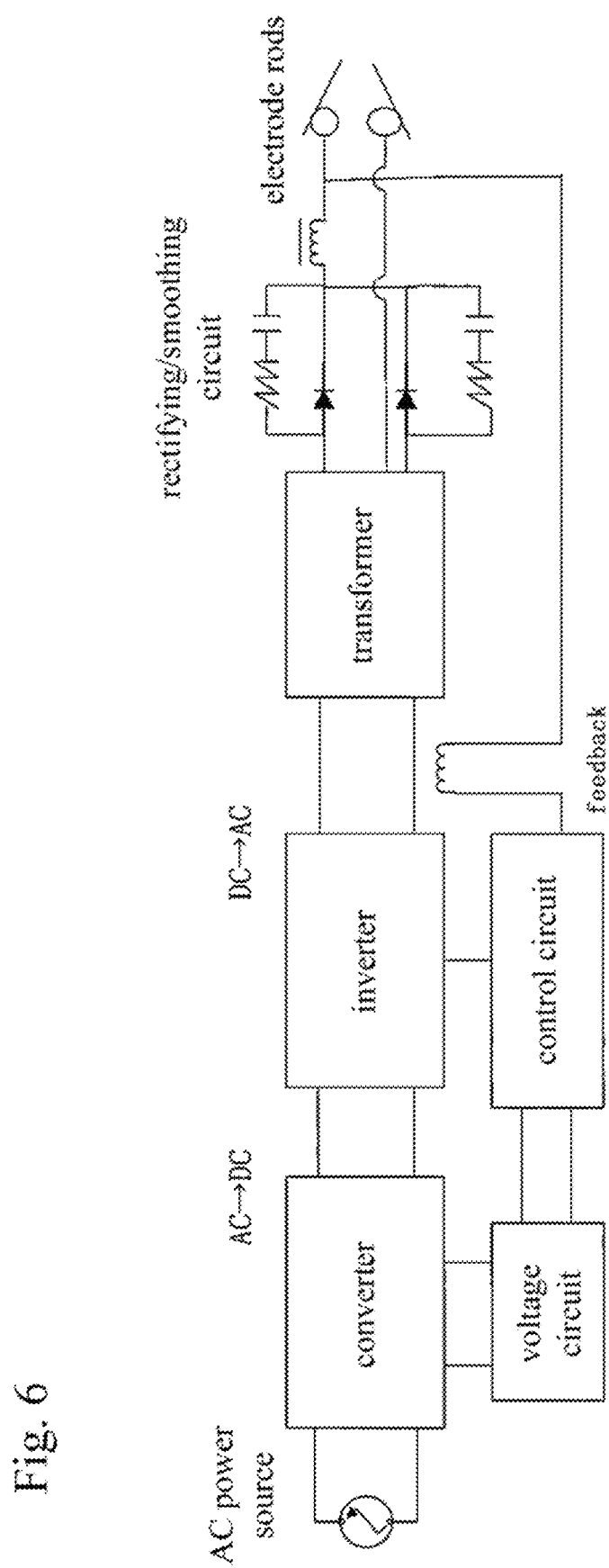
FIG. 6 is a block diagram showing an outline of an electric circuit used in the present invention.
Figure 7:
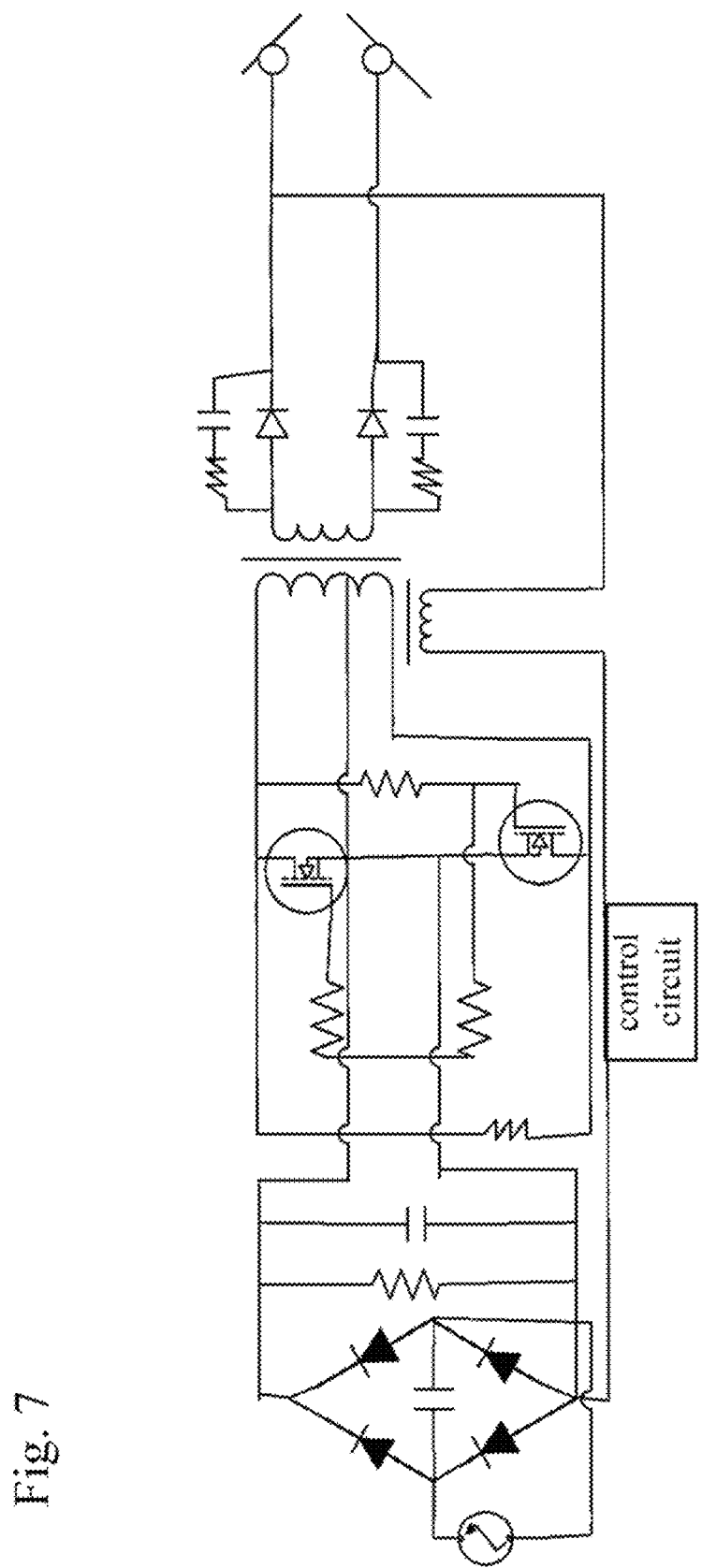
FIG. 7 is a circuit diagram of the electric circuit using MOSFET.
Figure 8:
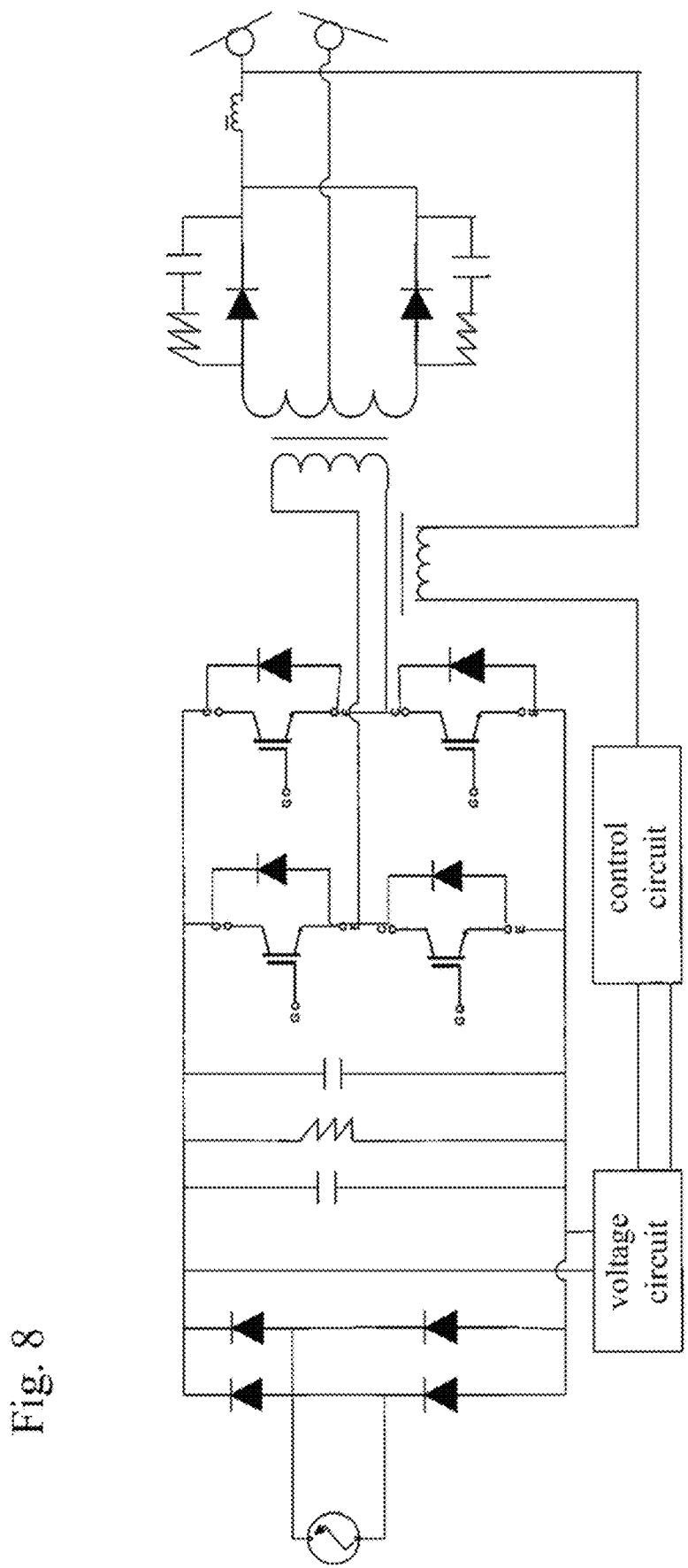
FIG. 8 is a circuit diagram of the electric circuit using IGBT.

Then, the electric circuit installed in the body portion 30 of the light therapy device 1 will be explained. FIG. 6 is a block diagram showing the outline of the electric circuit. As shown in FIG. 6, the electric circuit of the present invention is formed by a converter, an inverter, a transformer and a rectifying/smoothing circuit as a basic structure. A control circuit and a voltage circuit are incorporated in the above described basic structure. For the converter, as a circuit as simple as possible, it is preferable to use a diode-capacitor circuit or a four diode-capacitor rectifier circuit using a large capacity capacitor and diode. For the inverter, a circuit using MOSFET (Metal-Oxide-Semiconductor Field-Effect Transistor) shown in FIG. 7 or IGBT (Insulated Gate Bipolar Transistor) shown in FIG. 8 can be used. In the IGBT circuit, two pairs of IGBTs are formed and AC (alternating current) components are generated by performing high speed switching. After the AC conversion is performed by a high-frequency transformer, the rectification and the smoothing are performed using a diode and a choke coil. Thus, arc light can be stably obtained while suppressing pulsation. When a high-frequency rectifier circuit using MOSFET or IGBT is used, the light therapy device can be small-sized and light-weighted. For stabilizing the light generated by arc discharge, it is required to suppress the pulsation of the voltage and improve the rectification. This can be achieved by using MOSFET or IGBT enabling the high speed switching.

Figure 9:
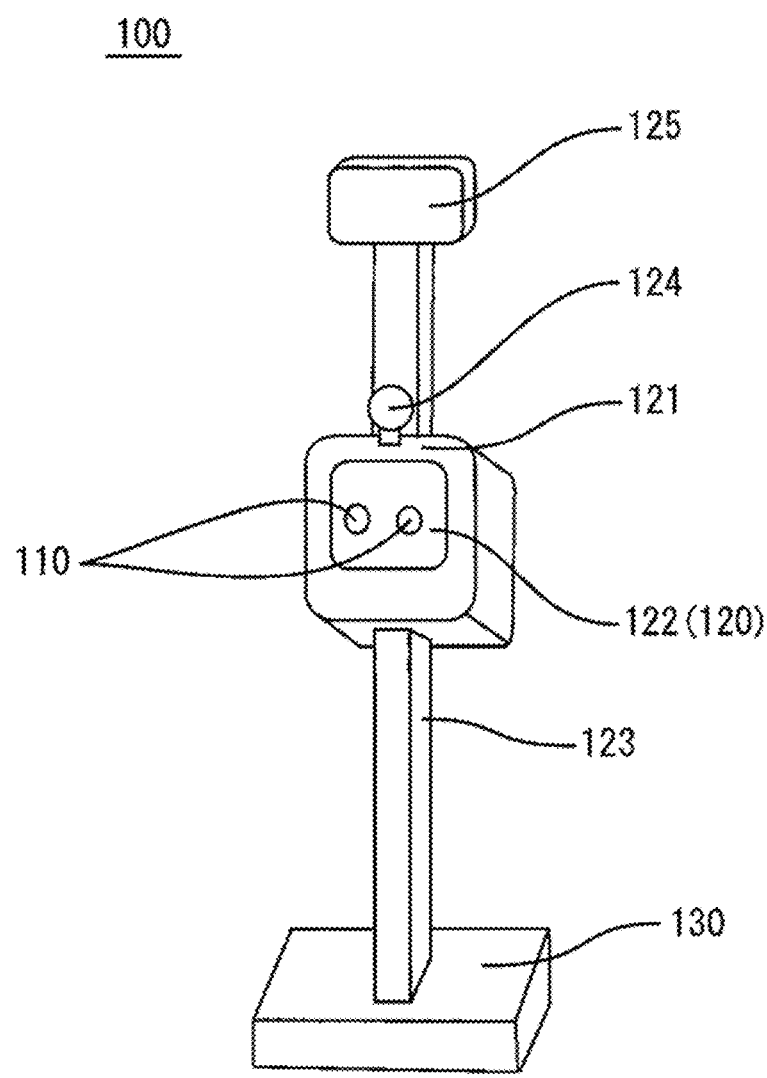
FIG. 9 is a perspective view showing another embodiment of the light therapy device.

FIG. 9 is a perspective view showing another embodiment of the light therapy device. A light therapy device 100 shown in FIG. 9 is a stationary type device. As shown in FIG. 9, the light therapy device 100 is formed by a pair of electrode rods 110, an irradiation portion 120 configured to be movable in the vertical direction and a body portion 130 housing an electric circuit and the like inside, for example. The explanation of the electrode rods 110 and the body portion 130 is omitted since the electrode rods 110 and the body portion 130 have the same configurations as the electrode rods 10 and the body portion 30 respectively. The irradiation portion 120 is formed by a hood 121 covering a part of the circumference of the electrode rods 110, a support portion 122 for supporting the electrode rods 110, a strut 123 for supporting the support portion 122 so as to be movable in the vertical direction, a sensor 124 for detecting the position of the user and a camera 125 for imaging the user, for example. The support portion 122 (including the hood 121 and other portions) is arranged so as to be movable in the vertical direction with respect to the strut 123. For example, the relative movement in the vertical direction is enabled by a rack and pinion system by providing the rack on the strut 123 and the pinion on the support portion 122. Since the motor is installed in the support portion 122, the pinion can be driven and rotated by electricity.

The sensor 124 is, for example, an ultrasonic sensor. The sensor 124 is mounted on the hood 121 of the irradiation portion 120. The sensor 124 detects whether or not the human body exists within a predetermined distance from the light therapy device 100. When the sensor 124 detects that the human body continuously exists for a predetermined time period or more, the motor installed in the support portion 122 is driven to move the support portion 122 in the vertical direction with respect to the strut 123. At that time, the support portion 122 is moved while detecting the distance between the sensor 124 and the human body. For example, the portion where the width of the human body suddenly narrows can be recognized as the neck of the human body. Consequently, even when the height and other conditions vary, the support portion 122 of the electrode rods 110 can be automatically moved to an optimum position.

It is also possible to combine an infrared sensor with the sensor 124. It is also possible to sense the temperature of the human body. Thus, the motor can be prevented from being erroneously driven when the object other than the human is detected. It is also possible to read the thermal image of the heat source directly using a thermography. Thus, the support portion 122 of the electrode rods 110 can be moved to the lower part of the head having a circular shape. It is also possible to photograph the head of the human body by using the camera 125 and analyzing it by an image recognition software. Thus, the support portion 122 of the electrode rods 110 can be moved to an optimum position. Although not illustrated, same as the light therapy device 1, the adsorption portion and the fan are installed inside the irradiation portion 120 of the light therapy device 100.

Figure 10:
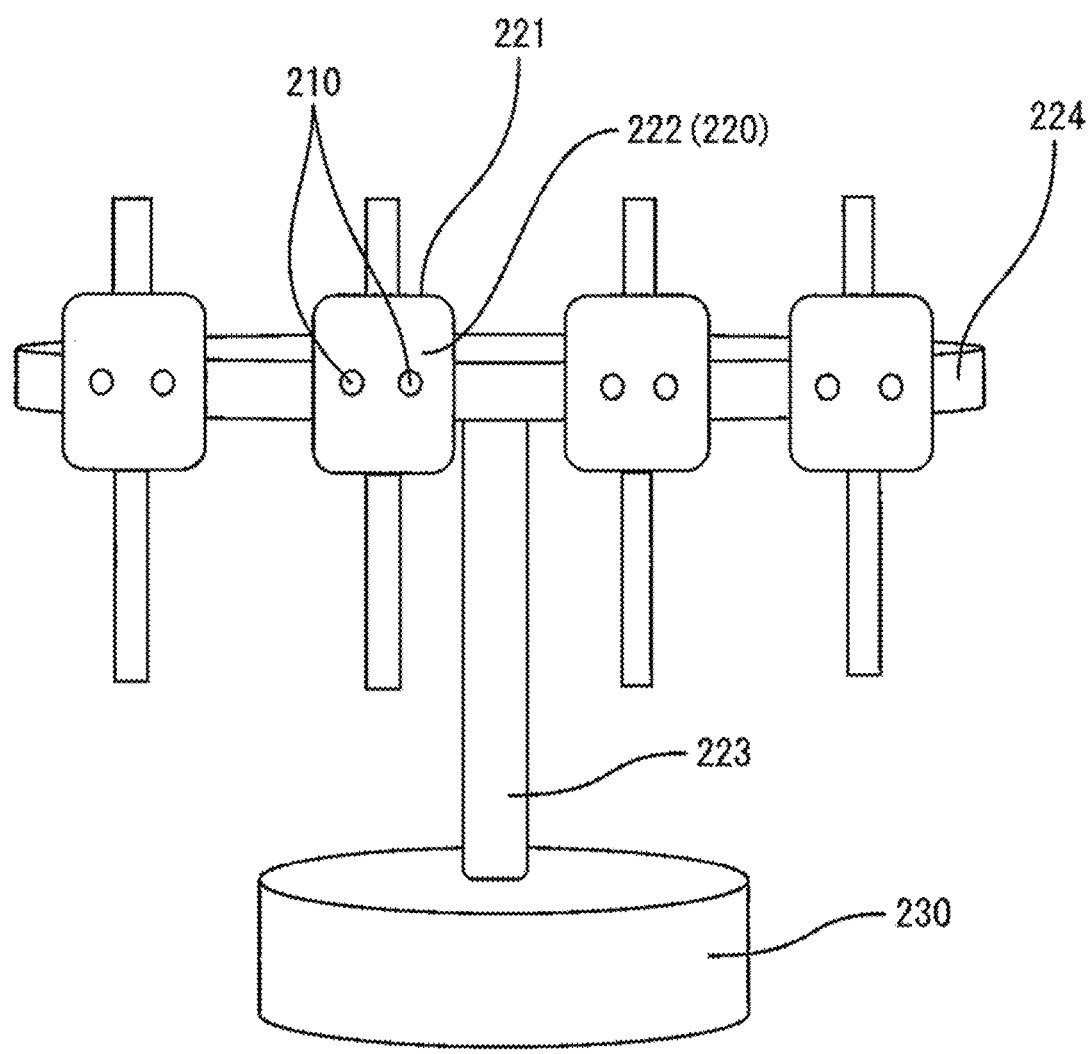
FIG. 10 is a perspective view showing another embodiment of the light therapy device.

FIG. 10 is a perspective view showing another embodiment of the light therapy device. As shown in FIG. 10, a light therapy device 200 is formed by a pair of electrode rods 210, an irradiation portion 220 configured to be movable in the vertical direction and a body portion 230 housing an electric circuit and the like inside, for example. The irradiation portion 220 is formed by a hood 221 covering a part of the circumference of the electrode rods 210, a support portion 222 for supporting the electrode rods 210, struts 223 for supporting the support portions 222 so as to be movable in the vertical direction and a holding portion 224 having a circular shape for supporting a plurality of struts, for example. The explanation of the electrode rods 210, the body portion 230, the hood 221 and the support portion 222 is omitted since the electrode rods 210, the body portion 230, the hood 221 and the support portion 222 have the same configurations as the electrode rods 110, the body portion 130, the hood 121 and the support portion 122 respectively. The light therapy device 200 includes a plurality of irradiation portions 220. Thus, the light therapy device 200 is configured to be used by a plurality of users simultaneously.

Since the struts 223 are arranged at a plurality of positions by the holding portion 224, a plurality of irradiation portions 220 can be arranged at a predetermined interval. Although not illustrated, same as the light therapy device 100, the light therapy device 200 can include a sensor and a camera. When the sensor and the camera are used, the positions of the irradiation portion 220 can be adjusted in accordance with the height of the plurality of users, for example. Although not illustrated, same as the light therapy device 1, the adsorption portion and the fan are installed inside the irradiation portion 220 of the light therapy device 200.

Figure 11:
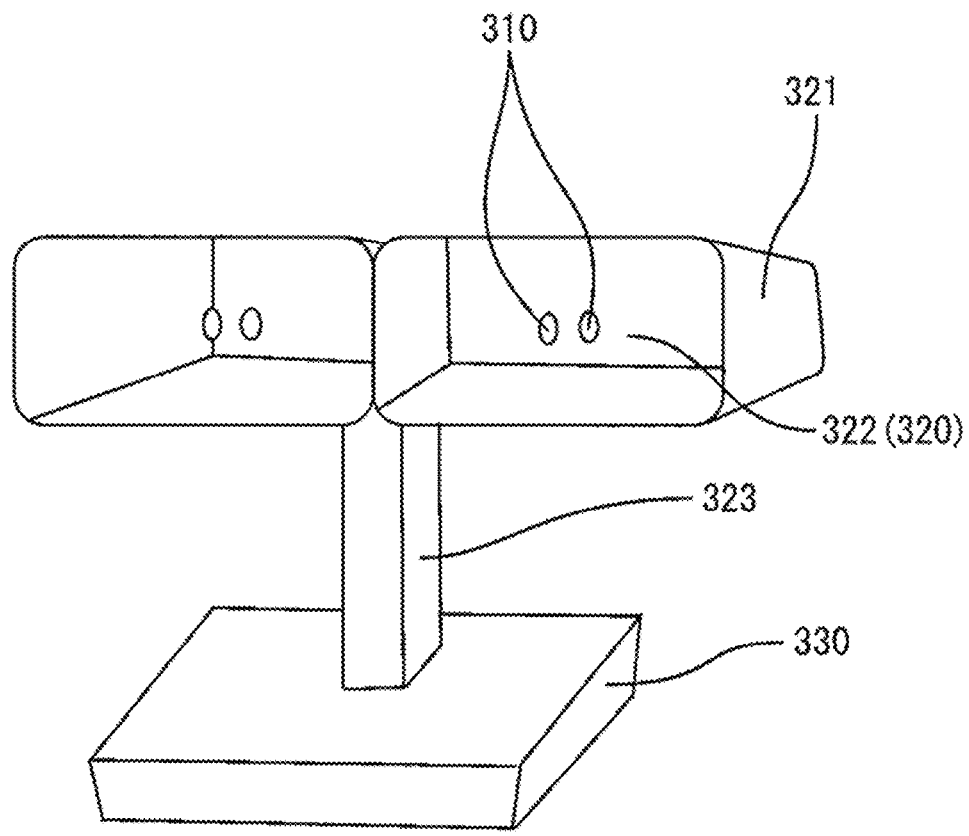
FIG. 11 is a perspective view showing another embodiment of the light therapy device.

FIG. 11 is a perspective view showing another embodiment of the light therapy device. As shown in FIG. 11, a light therapy device 300 is formed by a pair of electrode rods 310, an irradiation portion 320 configured to be movable in the vertical direction and a body portion 330 housing an electric circuit and the like inside, for example. The irradiation portion 320 is formed by a hood 321 covering a part of the circumference of the electrode rods 310, a support portion 322 for supporting the electrode rods 310 and a strut 323 for supporting the support portion 322 so as to be movable in the vertical direction, for example. The explanation of the electrode rods 310 and the body portion 330 is omitted since the electrode rods 310 and the body portion 330 have the same configurations as the electrode rods 110 and the body portion 130 respectively. In the light therapy device 300, the hood 321 of the irradiation portion 320 is opened in an approximately rectangular shape and the opening portion has a large area. Consequently, it is possible to irradiate the entire body of the user widely at once. It is also possible to share one irradiation portion 220 with a plurality of users. Although FIG. 11 shows the example of including two support portions 322 (hoods 321), it is also possible to arrange three or more support portions 322 (hoods 321). Although not illustrated, same as the light therapy device 100, the light therapy device 300 can include a sensor and a camera. When the sensor and the camera are used, the positions of the irradiation portion 320 can be adjusted in accordance with the height of the user, for example. Although not illustrated, same as the light therapy device 1, the adsorption portion and the fan are installed inside the light therapy device 300.

Figure 12:
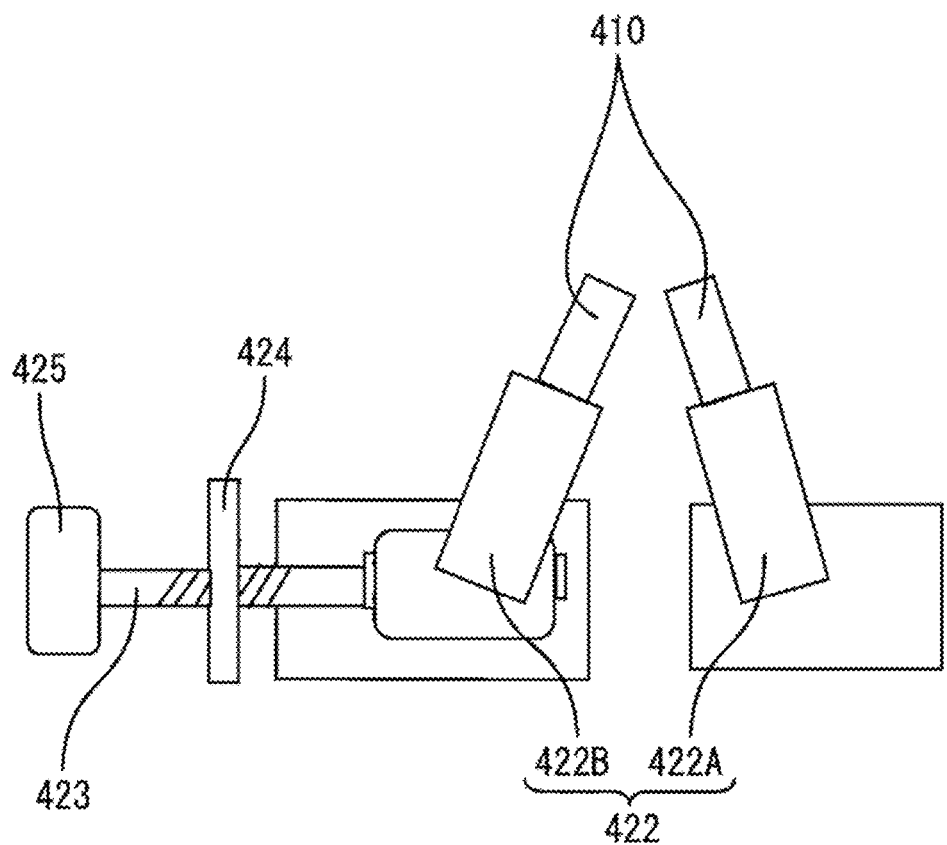
FIG. 12 is a plan view showing another embodiment of a support portion.

FIG. 12 is a plan view showing another embodiment of the support portion. As shown in FIG. 12, a support portion 422 is formed by a pair of support portions 422A, 422B for independently supporting a pair of electrode rods 410. The position of the support portion 422A is fixed, while the support portion 422B is configured to be movable in the direction of approaching to the support portion 422A and the direction of separating from the support portion 422A. Consequently, the distance (light source distance) between the pair of electrode rods 410 can be optimally adjusted. The support portions 422A, 422B are arranged in an angled state so that the support portions 422A, 422B approach to each other toward the tip end side of the electrode rods 410. A screw thread is formed on a shaft 423 connected to the support portion 422B. The shaft 423 is inserted into a screw hole formed on a fixing portion 424. The shaft 423 is rotated with respect to the fixing portion 424 by rotating an adjustment knob 425 fixed to the tip end of the shaft 423. Consequently, the support portion 422B can be relatively rotated with respect to the support portion 422A. Since the light source distance can be changed, the intensity of the light can be adjusted or the distance between the pair of electrode rods 420 can be shortened at the time when the consumption of the electrode rods 410 is advanced, for example. It is also possible to form an automatic adjustment mechanism for electrically moving the support portion 422B by installing a motor, for example. If the structure of moving both left and right support portions is adopted, there is a risk of the occurrence of short circuit between the support portions when high voltage is applied in a state that the left and right support portions are connected. The short circuit between the support portions can be prevented by adopting the configuration of moving only one of the support portions.

Figure 13:
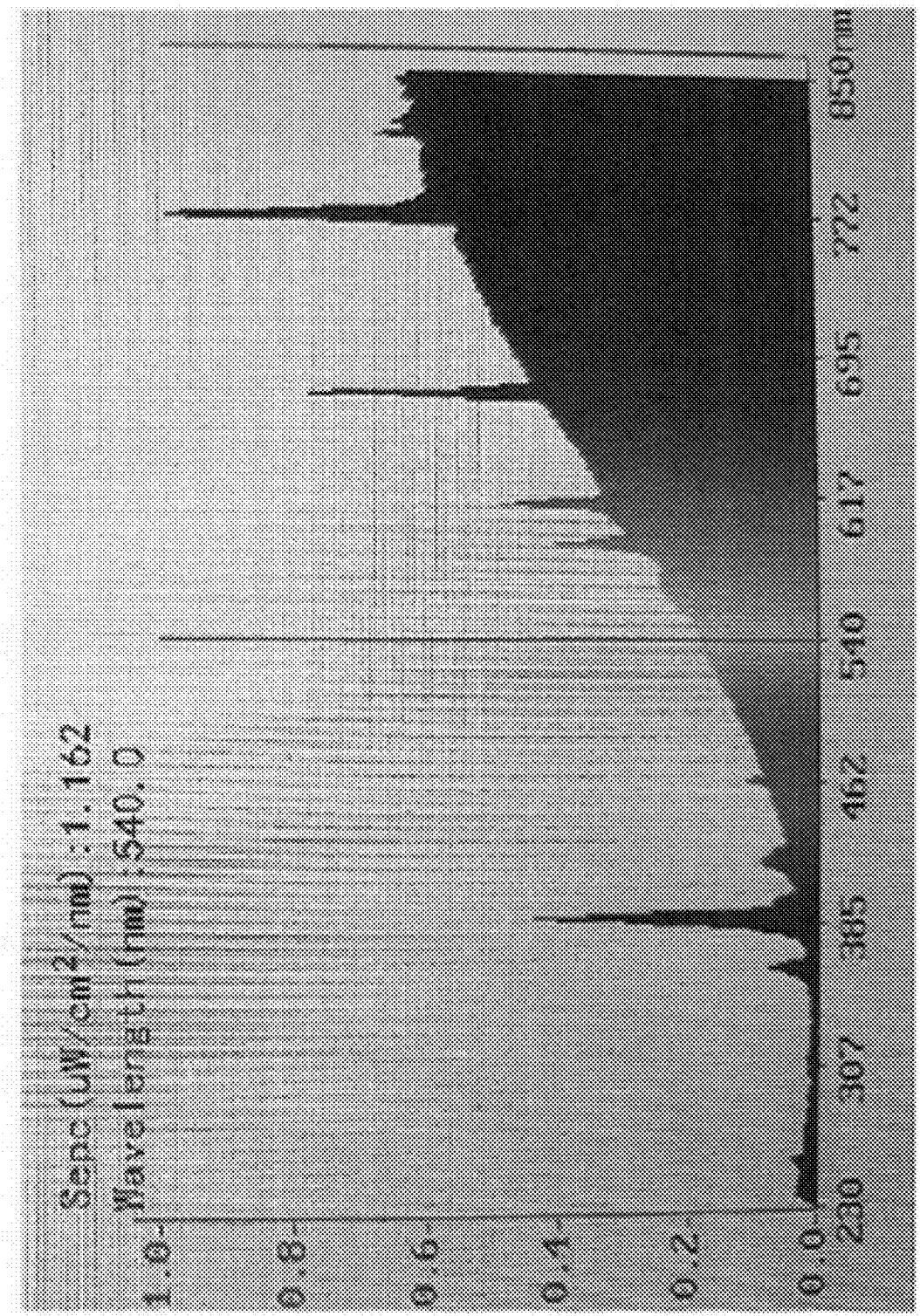
FIG. 13 is a spectrum of light using a conventional electrode rod.

Then, the relation between the components of the electrode rod and the wavelength of light emitted from the light therapy device. FIG. 13 shows the spectrum of light emitted from the light therapy device in the case of using a conventional electrode rod composed mainly of potassium and iron. FIG. 13 shows a result of measuring the wavelength of light emitted by arc discharge using a light wavelength measurement device (OHSP350C and 350UV) manufactured by Hangzhou Hopoo Light & Color Technology Co., Ltd. within the region between 230 nm to 850 nm. The horizontal axis shows the wavelength (nm) and the vertical axis shows the intensity of light emission of each wavelength. As shown in FIG. 13, when the conventional electrode rod is used, the emission peak appears near 385 nm caused by potassium and the emission peak appears near 650 nm caused by iron. Both emission peaks are within the visible light region (380 nm to 780 nm). In addition, low wavelength appears in the ultraviolet region (less than 380 nm).

Figure 14:
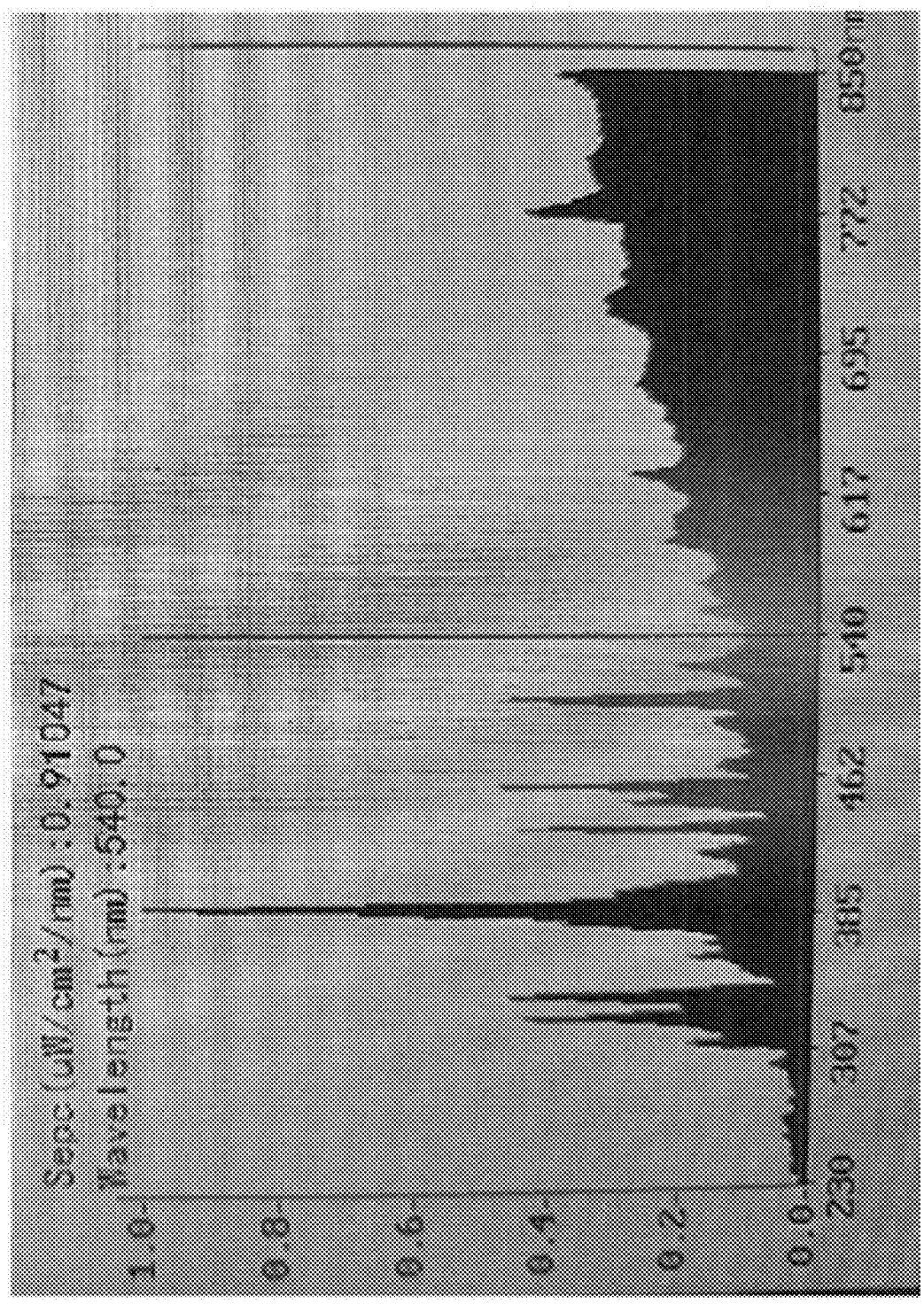
FIG. 14 is a spectrum of light in a case adding titanium nitride.

FIG. 14 shows the spectrum of light emitted from the light therapy device in the case of adding titanium nitride (TiN) to the conventional electrode rod. When titanium nitride was added, the light intensity of the ultraviolet rays could be suppressed while covering the ultraviolet region. In addition, the number of the emission peaks could be increased and the width of the peaked wavelength region could be extended in the emitted light. This is because titanium nitride has a hard property in various titanium compounds and titanium nitride has a property of absorbing the visible light and the light of the ultraviolet region. Thus, absorption effect and scattering effect of light occur. Therefore, the emission peak newly appears on the short wavelength side and long wavelength side of near 385 nm which is the emission spectrum peculiar to potassium as shown in FIG. 14. Especially, the number of the emission peaks was increased in the visible region of 500 nm or less and the peaked wavelength region was extended. It was confirmed that the scattering effect also occurred in all wavelength regions by increasing the amount of titanium nitride to be added. When the amount of titanium nitride to be added was small, arc discharge was generated on an aggregate of several kinds of metallic elements in the core material portion of the electrode rod. In this process, the collective oscillations are excited by the free electrons on the surfaces of the metal particles and the other mixed elements interacting with rays of light, and then surface plasmon resonance and light diffraction cause the transfer of the fluorescence resonance energy and the occurrence of light emission from several energy levels. As a result, the light emission is found to be enhanced at the long wavelength side and the number of the emission peaks was increased.

Figure 15:
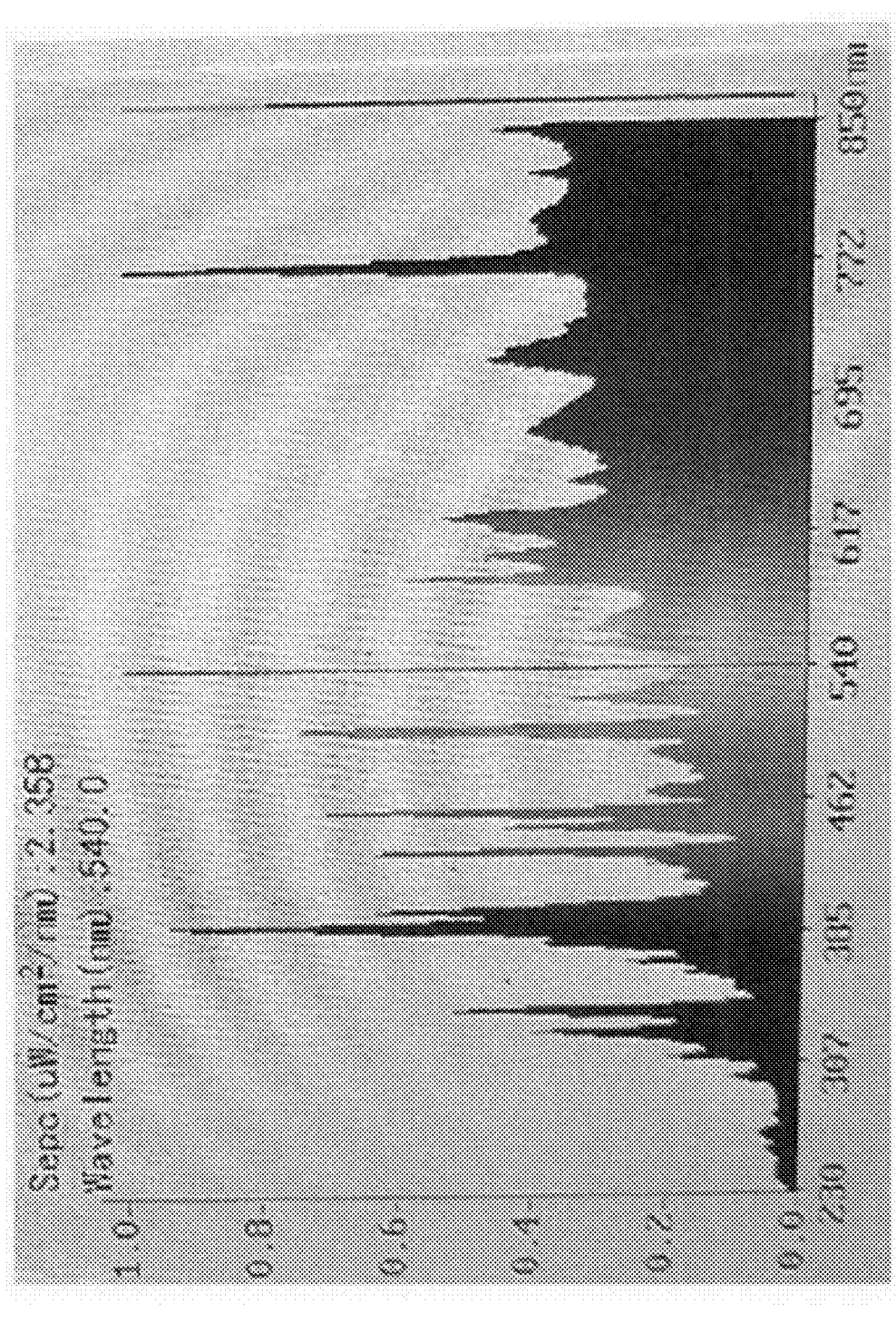
FIG. 15 is a spectrum of light in a case adding titanium nitride and calcium.

FIG. 15 shows the spectrum of light emitted from the light therapy device in the case of adding titanium nitride (TiN) and calcium (Ca) to the conventional electrode rod. When calcium was added, the intensity of light was found to be increased at the near infrared region (near 600 nm). As the amount of added titanium nitride was increased, the whole intensity of light was reduced by the amount of absorbed light. When a small amount of calcium compound was added, the whole intensity of light could be enhanced. The emission intensity was increased as the added calcium compound, which had the emission spectrum in the visible light region, was increased. The emission intensity could be increased up to approximately five times.

Figure 16:
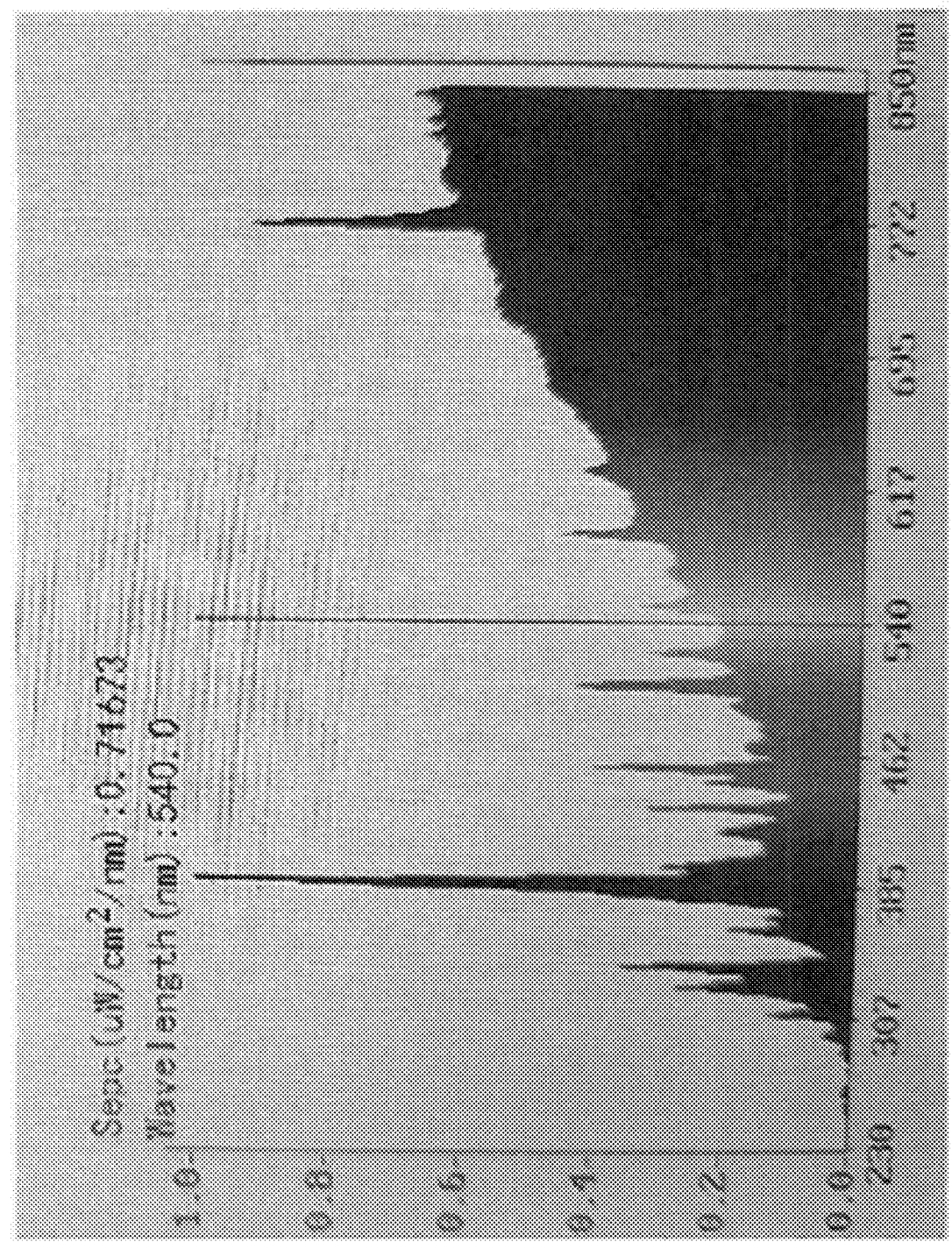
FIG. 16 is a spectrum of light in a case adding titanium nitride and silver.

FIG. 16 shows the spectrum of light emitted from the light therapy device in the case of adding titanium nitride (TiN) and silver (Ag) to the conventional electrode rod. When silver was added, the enhancing effect of the emission intensity could be seen widely in the region from the visible light of 500 nm or more to the infrared region. It was also found that the effect of reducing the ultraviolet region (UV-A and UV-B) was remarkable although not a little ultraviolet region appeared when only titanium nitride was added. Table 3 shows the case where the electrode rod contains potassium and UV-B and UV-C which are harmful to a biological body can be reduced to the level extremely near to zero by adding silver and calcium.

TABLE 3

| electrode rod material | ultraviolet intensity (uW/cm$^2$) | | | |
|---|---|---|---|---|
| | UV-A | UV-B | UV-C | sum |
| titanium nitride + potassium | 58.9 | 5.6 | 3.0 | 67.5 |
| titanium nitride + potassium + silver + calcium | 19.4 | 0.4 | 0 | 19.8 |

Then, the experiment result for confirming the effect of the adsorbent is shown. The gas generated when the electrode rod was combusted by arc discharge for 1 minute and 30 seconds was sucked into a syringe of 160 cc, the syringe was connected to another syringe containing 30 cc of the adsorbent and the sucking operation and the pushing operation of the pump were repeated ten times. As for each of the five kinds of the adsorbents, the result of measuring the contained amount of carbon dioxide using a carbon dioxide detector tube is shown in FIG. 4.

TABLE 4

| No. | adsorbent material | carbon dioxide amount before adsorption | carbon dioxide amount after adsorption |
|---|---|---|---|
| 1 | charcoal + zeolite (crushed) + silica gel + water | 3000 ppm | 1800 ppm |
| 2 | 1 + lignin | 3000 ppm | 2500 ppm |
| 3 | 1 + ash | 3000 ppm | 1500 ppm |
| 4 | 1 + ash + feldspar | 3000 ppm | 500 to 600 ppm |
| 5 | 4 + alkaline electrolytic water (instead of water) | 3000 ppm | 300 ppm (minimum) |

As shown in Table 4, the carbon dioxide concentration in the collected gas generated by combustion was 3000 ppm. When the adsorbent containing only charcoal, zeolite, silica gel and water were used, the carbon dioxide concentration was improved to 1800 ppm. When the adsorbent further containing ash was used, the carbon dioxide concentration was improved to 1500 ppm. When the adsorbent further containing the feldspar was used, the carbon dioxide concentration was significantly improved to 500 to 600 ppm. When the adsorbent further containing the alkaline electrolytic water was used, the carbon dioxide concentration was improved to 300 ppm which is 1/10 (one-tenth). By using the above described carbon dioxide adsorbent capable of obtaining significant effect safely, the light therapy device can be used while significantly reducing load to environment caused by the combustion of the electrode rod. Furthermore, without being limited to the field of the light therapy device, the carbon dioxide adsorbent can be used for the purpose of reducing carbon dioxide. As for the materials of the adsorbent, the adsorption rate is the highest when the adsorbent is manufactured by mixing ash and feldspar powder into the crushed charcoal and zeolite, adding a small amount of water, alkaline electrolytic water and silica gel and stirring the mixture to have viscosity and water holding property. Regarding the kind of the feldspar, potassium feldspar, soda feldspar, Indian feldspar, pottery stone and the like can be listed. Regarding an example of the components of the feldspar, the feldspar can include $SiO_2$: 60 to 66%, $Al_2O_3$: 18 to 24%, CaO: 0.1 to 0.3%, MgO: 0.01 to 0.04%, $K_2O$: 5 to 12% and $Na_2O$: 3 to 5%, for example. The electrolytic water means the substance generated at the negative side when water is electrolyzed.

Then, the experiment result for confirming the effect of the optical energy enhancing mechanism of the present invention is shown. Table 5 shows the experiment result comparing the light intensity when the optical energy enhancing mechanism is used. Using a flat plate having a size of 100 mm×100 mm×1 mm, a plate formed by arranging a plate made of stainless (SUS304) on the flat plate, a plate further forming vertical grooves on the plate made of stainless and a plate further forming vertical and horizontal grooves of the stainless were compared with the plate without the stainless. Regarding the metal plate having only the vertical grooves, totally 55 grooves having the width of 0.1 mm and the depth of 0.5 mm were formed within the range of the length of 100 mm and the width of 35 mm approximately at the center of the metal plate. Regarding the metal plate having the vertical and horizontal grooves, totally 55 vertical grooves having the width of 0.1 mm and the depth of 0.5 mm were formed within the range of the length of 100 mm and the width of 35 mm approximately at the center of the metal plate and totally 20 horizontal grooves having the same width and depth as the vertical grooves were formed within the range of the length of 40 mm where the vertical grooves were formed. The light intensity of the reflected light was measured when the flat plate was arranged near the irradiation portion and the light was irradiated. The unit of the values is shown by lux (lx).

TABLE 5

| No. | without stainless | stainless | stainless + vertical grooves | stainless + vertical and horizontal grooves |
|---|---|---|---|---|
| 1 | 1723 | 1988 | — | — |
| 2 | 2563 | — | 4125 | — |
| 3 | 2399 | — | 4473 | — |
| 4 | 1682 | — | 4014 | — |
| 5 | 2399 | — | 6036 | — |
| 6 | 3318 | — | — | 10690 |
| 7 | 2684 | — | — | 21190 |
| 8 | 1684 | — | — | 16060 |

As shown in FIG. 5, when the plate made of the stainless was arranged, it was confirmed that the light intensity was increased. In addition, when the vertical grooves or the vertical and horizontal grooves were formed on the stainless plate, it was confirmed that the light intensity was further increased. When the vertical and horizontal grooves were formed, the light intensity was increased approximately three times to ten times stronger than the case where the stainless was not arranged.

Then, the experiment of the therapeutic effect was performed by using the light therapy device of the present invention for the patients of the infection. The evaluation was performed for the group of patients who developed respiratory symptoms (e.g., runny nose, cough, phlegm, sneeze, pharyngeal pain) acutely and further grouped by existence or absence of fever. In addition, the inventor focused on a differential leukocyte count in blood sampling. In case of bacterial infection, the leukocyte and CRP (inflammation reaction) increase in accordance with the degree of severity. However, the inventor focuses on the fact that the leukocyte and CRP does not increase in general in case of viral infection. Thus, the inventor focuses on the left shift of the differential leukocyte count. The inventor focuses on the fact that the increment of the number of lymphocytes (decrement of the number of neutrophils) can be seen in the differential leukocyte count in case of the viral infection, while the increment of the number of neutrophils (decrement of the number of lymphocytes) can be seen in case of the bacterial infection. In addition, when the bacteria and the virus were identified by culture results of the sputum examination, the process was also evaluated.

Table 6 shows the normal ranges of the number of neutrophils and the number of lymphocytes.

TABLE 6

|  | male | female |
|---|---|---|
| normal range of number of neutrophils | 45.2 to 68.8% | 49.7 to 72.7% |
| normal range of number of lymphocytes | 26.8 to 43.8% | 24.5 to 38.9% |

As Experiment 1, forty patients of the age group of 30s to 80s with symptom of acute respiratory infection (e.g., runny nose, cough, phlegm, sneeze, pharyngeal pain, chill) were grouped into twenty patients having a fever of 37.5 or more and twenty patients without a fever, and a neck to an anterior chest and a right upper abdomen at which a liver was located were irradiated with light using the light therapy device of the present invention twice or three times per day, three to ten minutes each time. The twenty patients without a fever seemed to be an extremely early stage of bacterial or viral infectious disease since the differential leukocyte count obtained by blood sampling was within a normal range. The symptom disappeared in all twenty patients after the irradiation was performed by the light therapy device for two days. In twenty patients having a fever of 37.5 or more, ten patients whose neutrophils was recognized to be increased in the differential leukocyte count seemed to be an early stage of bacterial infection and CRP was increased to 0.4 to 7. Six patients whose lymphocytes were increased seemed to be an early stage of viral infection. Four patients whose differential leukocyte count was within the normal range seemed to be an extremely early stage of infection. The light therapy device of the present invention was used for the above described patients for two to five days. The fever was reduced to the normal temperature within two to three days for fourteen patients among twenties. The fever was reduced to the normal temperature within four to five days for the rest six patients. The respiratory symptom (e.g., runny nose, cough, phlegm, sneeze, pharyngeal pain, chill) disappeared within two days for eight patients, disappeared within three days for six patients and disappeared within four to five days for the rest six patients. In addition, the blood sampling data was recognized to be normalized within one week to ten days. It was suggested that the patient had bacterial infections when the number of neutrophils was increased while the patient had the viral infectious disease when the number of lymphocytes was increased. The improvement effect was remarkable for non-serious patients in an extremely early stage of respiratory symptom or patients without a fever. The symptom disappeared within one day in many cases and the symptom was improved within two days in all patients. In addition, it was confirmed that the improvement effect increased when the light therapy device was continuously used every day in case of fever. The effect could be recognized earlier as the light therapy device used earlier.

As Experiment 2, for total three patients comprised of two patients who were positive (1+ to 2+) for MRSA (Methicillin-resistant *Staphylococcus aureus*) for six months in the test result of cultivating bacteria from the throat and one patient who was positive (1+) for MRSA for three months, a neck to an anterior chest and a right upper abdomen were irradiated with light using the light therapy device of the present invention twice per day (morning and evening), five to ten minutes each time and for totally five days. A negative (−) of MRSA was confirmed for all three patients in the specimen of pharynx wiping liquid after seven days from the beginning of the irradiation.

As Experiment 3, four patients who were positive for PCR in saliva examination of SARS-CoV-2 were grouped into two patients having a fever of 37.5 or more and two patients without a fever, a neck to an anterior chest and a right upper abdomen were irradiated with light using the light therapy device of the present invention twice or three times per day, five to ten minutes each time and for totally five continuous days. A negative was confirmed for all four patients in the PCR test using the specimen of nasopharynx wiping liquid after five days from the beginning of the irradiation.

The inspection data of Experiments 1 to 3 was the analysis result analyzed in an examination center associated with a health institute. From Experiment 1, it was suggested that the patient had bacterial infections when the number of neutrophils was increased while the patient had the viral infectious disease when the change of the differential leukocyte count was little relative to the fever or when the number of lymphocytes was increased. It was confirmed that the improvement effect was remarkable and the symptom disappeared within several hours in many cases for non-serious patients in an extremely early stage of respiratory symptom or patients without a fever. The effect could be recognized earlier as the light therapy device used earlier. The symptom was recognized to be improved in many cases and the improvement was earlier even for the patients having a fever. From Experiments 2 and 3, it was confirmed that the present invention was also effective for MRSA and SARS-CoV-2.

As explained above, the conventional pattern of the emission peak can be changed by adding titanium nitride to the electrode rod. Although potassium has the emission peak at the visible light region, the emission peak can be also appeared on the short wavelength side of the original emission spectrum of potassium so that UV-A region is covered. Furthermore, the emission peaks can be increased in the pattern by using the absorption/scattering effect of light and plasmon effect caused by titanium nitride. The property of widely interfering and affecting the emission peak of other elements cannot be seen in the other elements and metal compounds other than titanium nitride. When titanium nitride is added, the light having the extended width of the wavelength region covering the ultraviolet region can be irradiated without adding other harmful metal elements having the emission spectrum in the ultraviolet region. Furthermore, when silver or calcium is added, the emission intensity can be enhanced at the near infrared region and the therapeutic effect to the biological body can be increased. It is considered that the biological body is affected by light near the infrared region around 600 nm to 900 nm which can be easily absorbed by the biological body. It is considered that the effects to the virus, the bacteria and the like are arisen from effective enhancement of the light emission where the emission spectrum is expanded to the short wavelength side from the original wavelength of the emission spectrum of potassium, the number of the emission peaks is increased, the near infrared region is used and the effect of the infrared rays is used. Consequently, the effect to the virus and bacterial infections can be exerted. In addition, when silver or calcium is added, the harmful ultraviolet wavelength of UV-B and UV-C can be reduced.

Although it is known that the ultraviolet rays have an effect of sterilizing the virus, the bacteria and the like, it is impossible for the human body to receive strong ultraviolet rays directly since the damage to skins and cells is too large. In the present invention, it is found that the effect can be exerted to the human body while necessary light of the ultraviolet region is reduced as much as possible by simultaneously using the light energy of the near infrared region which is easily absorbed by the human body. As a result of hyperthermic effect caused by the infrared rays generated by the combustion of carbon, physical reaction is accelerated and the light emission is effectively acted. In order to affect the pathogens ingested into the human body, strong light energy generated by arc discharge is required. Considering the fact that the ultraviolet intensity becomes too large and the harmful influence on the human body becomes large if the element having the emission peak at the ultraviolet region is used for obtaining light of the ultraviolet region and the fact that combusted substance brings the harmful influence generated by arc discharge to the human body, the element having the emission peak in the visible light region without having the emission peak in ultraviolet region is used. Thus, the emission peak is extended to the ultraviolet region and the light of the ultraviolet rays to be required can be minimalized and ensured to obtain the necessary effects.

The light therapy device of the present invention has the effect of preventing infection of the virus and the bacteria by the action of light energy having widely and effectively enhanced effective wavelength in addition to the thermal action and the activating action of organs caused by the infrared ray effect. Even after the bacteria and the virus are inhaled into the human body, the propagation in the human body can be prevented by using the light therapy device before the symptom appears. Thus, the development of the disease can be prevented if the stage is early. After the pathogens are increased by a large amount in the human body, the effect of reducing the number of pathogens and the effect of accelerating the improvement can be obtained after the disease. For the purpose of preventing the disease or before developing the disease, the effect can be obtained by using the light therapy device on the neck to the anterior chest for several ten seconds to several minutes once or twice a day when returning home from outside. After the disease is developed, it is preferable to irradiate the whole body as wide as possible especially on the anterior chest and the right upper abdomen at which a liver was located for several minutes to fifteen minutes twice to four times a day.

Carbon dioxide is generated when combusting carbon (e.g., black charcoal) which occupies a large part of the composition of the electrode rod. It is not preferable to discharge carbon dioxide as it is from a viewpoint of environmental pollution. In addition, the oxide of metal generated by the combustion generates odor and may cause harmful influence on the human body if it is inhaled into the user. It is achieved that the above described problem can be reduced by using the adsorbent containing clay powder, wood ash, charcoal and zeolite. Since carbon dioxide and the oxide of metal generated by combustion are adsorbed by the adsorbent, the user is suppressed from inhaling the generated substances directly. Furthermore, since the fan is driven by using the thermoelectric cooler, the adsorption of carbon dioxide and the oxide of metal to the adsorbent can be facilitated.

MOSFET or IGBT is used for the electric circuit of the light therapy device. In the conventional light therapy device, large-sized and heavy transformer is used. Thus, the electric circuit can be small-sized and light-weighted by using MOSFET or IGBT. Consequently, the light therapy device can be portable. In addition, the conventional large-sized transformer is subject to a usage environment such as a heat generation in a coil, a temperature and a humidity and thus not suitable for the public use devices which can be frequently used for a long time. Furthermore, the conventional device has disadvantages that there is a safety problem such as a risk of overvoltage depending on the usage environment and there is a large loss of secondary power of the transformer caused by iron loss or copper loss. The present invention solves the above described problems by using MOSFET or IGBT.

When a reflector made of metal is arranged near the light source and the grooves are formed on the reflector, the intensity of light can be enhanced. By adopting the above described configurations, the light can be generated with the minimum electric power. In addition, the light therapy device can be used even when the object is separated from the irradiation portion. For example, this is effective when irradiating farm animals and other animals with the light or irradiating large animals having thick skin with the light. In addition, this may be effective when strong light energy is required for repelling the virus and the like if such virus appears.

The usage of the light therapy device of the present invention is not limited to a personal use and usage in the hospital or the like. The light therapy device can be installed and publically used in the place where many people gather. For example, the light therapy device can be installed in transportation facilities (e.g., airport, train), buildings, commercial facilities, concert halls and sports watching sites. For example, when all passengers are irradiated with the light at a boarding gate or the like of an airplane, the spread of the infection in the airplane is prevented and the entrance of the pathogens from abroad can be suppressed. Namely, the spread of the infection caused by the movement of people is prevented. Thus, it is considered that the light therapy device has an effect of suppressing the infection spread regionally or pandemically. In addition, different from drugs and vaccines, there is no restriction on the type of the bacteria and the virus. The similar effect can be expected also for variable species and resistant bacteria hardly appear. Furthermore, the effect can be also expected for contagious diseases of farm animals and other animals other than the human.

The present invention is not limited to the embodiments of the light therapy device. The present invention can be also carried out as the electrode rod used for the pair of electrodes containing titanium nitride in the light therapy device.

The mixing ratio of the material of the core material portion of the electrode rod shown in the above described embodiments is merely an example. The configuration of the present invention is not limited to the above described ratio. In addition, the adsorbent of the electrode rod is merely an example. The configuration of the present invention is not limited to the above described ratio. The mixing ratio of the adsorbent is adjusted so as to keep viscosity and water holding property as a guideline. In the present invention, the names of the substance such as iron and calcium are the concept including the compounds such as iron compounds and calcium compounds.

Note that this invention is not limited to the above-mentioned embodiments.

Although it is to those skilled in the art, the following are disclosed as the one embodiment of this invention.

Mutually substitutable members, configurations, etc. disclosed in the embodiment can be used with their combination altered appropriately.

Although not disclosed in the embodiment, members, configurations, etc. that belong to the known technology and can be substituted with the members, the configurations, etc. disclosed in the embodiment can be appropriately substituted or are used by altering their combination.

Although not disclosed in the embodiment, members, configurations, etc. that those skilled in the art can consider as substitutions of the members, the configurations, etc. disclosed in the embodiment are substituted with the above mentioned appropriately or are used by altering its combination.

DESCRIPTION OF THE REFERENCE NUMERALS 1, 100, 200, 300 . . . light therapy device; 10, 110, 210, 310, 410 . . . electrode rod; 11 . . . core material portion; 12 . . . aggregate material portion; 20, 120, 220, 320 . . . irradiation portion; 21, 121, 221, 321 . . . hood; 22, 122, 222, 322, 422 . . . support portion; 23 . . . fan; 24 . . . thermoelectric cooler; 25 . . . adsorption portion; 30, 130, 230, 330 . . . body portion

The invention claimed is:

1. A light therapy device, comprising:
a pair of electrodes containing carbon, titanium nitride and at least one of potassium and potassium compounds;
a support portion for supporting the pair of electrodes so that the pair of electrodes is arranged at a predetermined distance from each other; and
an electric circuit configured to apply a voltage between the pair of electrodes for generating arc discharge between the pair of electrodes.

2. The light therapy device according to claim 1, wherein the pair of electrodes further containing at least one of silver and calcium.

3. The light therapy device according to claim 1, further comprising:
an adsorbent configured to adsorb carbon dioxide generated by the arc discharge, wherein
the adsorbent contains clay powder, wood ash, charcoal and zeolite.

4. The light therapy device according to claim 3, further comprising:
a fan installed in a vicinity of the pair of electrodes for introducing the carbon dioxide to the adsorbent.

5. The light therapy device according to claim 1, wherein the electric circuit includes a MOSFET or an IGBT.

6. The light therapy device according to claim 1, further comprising:
a reflector made of metal for reflecting a light generated by the arc discharge, wherein
a groove is formed on the reflector.

7. An electrode rod used for the pair of electrodes of the light therapy device of claim 1, wherein
the electrode rod contains carbon, titanium nitride and at least one of potassium and potassium compounds.

* * * * *